(12) United States Patent
Wolleschensky

(10) Patent No.: US 7,298,551 B2
(45) Date of Patent: Nov. 20, 2007

(54) METHOD AND ARRANGEMENT FOR CHANGING THE SPECTRAL COMPOSITION AND/OR INTENSITY OF ILLUMINATION LIGHT AND/OR SPECIMEN LIGHT IN AN ADJUSTABLE MANNER

(75) Inventor: Ralf Wolleschensky, Apolda (DE)

(73) Assignee: Carl Zeiss Jena GmbH, Jena (DE)

( * ) Notice: Subject to any disclaimer, the term of this patent is extended or adjusted under 35 U.S.C. 154(b) by 0 days.

(21) Appl. No.: 10/654,702

(22) Filed: Sep. 4, 2003

(65) Prior Publication Data

US 2004/0159797 A1 Aug. 19, 2004

(30) Foreign Application Priority Data

Sep. 4, 2002 (DE) .................................. 102 41 472

(51) Int. Cl.
*G02B 21/06* (2006.01)
(52) U.S. Cl. ........................................ 359/386; 359/495
(58) Field of Classification Search ................ 359/495, 359/618, 386, 246, 256, 629, 634; 356/364, 356/365
See application file for complete search history.

(56) References Cited

U.S. PATENT DOCUMENTS

| | | | | | |
|---|---|---|---|---|---|
| 4,767,188 | A | * | 8/1988 | Myer | 359/503 |
| 5,304,810 | A | * | 4/1994 | Amos | 250/458.1 |
| 5,414,540 | A | * | 5/1995 | Patel et al. | 349/196 |
| 5,867,604 | A | * | 2/1999 | Ben-Levy et al. | 382/254 |
| 6,285,500 | B1 | * | 9/2001 | Ranalli et al. | 359/497 |
| 6,529,307 | B1 | * | 3/2003 | Peng et al. | 359/256 |
| 6,867,919 | B2 | * | 3/2005 | Seyfried | 359/618 |
| 2002/0122251 | A1 | * | 9/2002 | DeBoynton et al. | 359/484 |
| 2003/0058516 | A1 | * | 3/2003 | Scott et al. | 359/246 |

FOREIGN PATENT DOCUMENTS

| | | |
|---|---|---|
| DE | 197 02 753 | 1/1997 |
| EP | 977 069 | 2/2000 |
| WO | WO 9835251 A1 * | 8/1998 |

OTHER PUBLICATIONS

Pawley, "Handbook of Biological Confocal Microscopy"; Plenum Press 1995.
Corle, Kino, "Confocal Scanning, Optical Microscopy and Related Imaging Systems"; Academic Press 1996.

(Continued)

*Primary Examiner*—Arnel Lavarias
(74) *Attorney, Agent, or Firm*—Reed Smith LLP

(57) ABSTRACT

Method and arrangement for changing the spectral composition and/or intensity of illumination light and/or specimen light in an adjustable manner, wherein a spatial separation into radiation components of different polarization is carried out with a first polarizing device, a spectral, spatial splitting of at least one radiation component is carried out with first dispersion device, the polarization state of at least one part of the spectrally spatially split radiation component is changed, and a spatial separation and/or combination of radiation components of different polarization are/is carried out by a second polarizing device, wherein a spatial combination of radiation components which are changed and not changed with respect to their polarization state is advantageously carried out by a second dispersion device.

31 Claims, 12 Drawing Sheets

OTHER PUBLICATIONS

T. Wilson, et al., "Method of obtaining sectioning by using structured light in a conventional microscope", *Optics Letters* 22 (24), 1997.

MicroWires by Moxtek, Inc., Orem, USA, ; (www.profluxpolarizer.com).

Stobrawa, et al., *Apl. Phy.* B72, 627-630 (2002).

"Flow Cytometry and Sorting", second edition, M. R. Melamed, T. Lindmo, M. L. Mendelsohn, eds., Wiley & Sons, Inc., New York, 1990, 81-107.

* cited by examiner

METHOD AND ARRANGEMENT FOR CHANGING THE SPECTRAL COMPOSITION AND/OR INTENSITY OF ILLUMINATION LIGHT AND/OR SPECIMEN LIGHT IN AN ADJUSTABLE MANNER

CROSS-REFERENCE TO RELATED APPLICATION

This application claims priority of German Application No. 102 41 472.6, filed Sep. 4, 2002, the complete disclosure of which is hereby incorporated by reference.

BACKGROUND OF THE INVENTION a) Field of the Invention

The invention is directed to a method in microscopy, particularly fluorescence microscopy, laser scanning microscopy, fluorescence correlation microscopy and scanning nearfield microscopy, for examining primarily biological specimens, preparations and associated components. This includes methods for screening active ingredients (high throughput screening) based on fluorescence detection. Simultaneous examinations of specimens with multiple fluorophores in real time by means of simultaneous illumination of the specimen at a plurality of points on the specimen are therefore possible with overlapping fluorescence spectra even in three-dimensional structures of thick specimens.

b) Description of the Prior Art

A typical area of application of light microscopy for the examination of biological preparations is fluorescence microscopy (Pawley, "Handbook of Biological Confocal Microscopy"; Plenum Press 1995). For this purpose, determined dyes are used for specific labeling of cell parts.

The irradiated photons having a determined energy excite the dye molecules, through the absorption of a photon, from the ground state to an excited state. This excitation is usually referred to as single-photon absorption (FIG. 1a). The dye molecules excited in this way can return to the ground state in various ways. In fluorescence microscopy, the most important transition is by emission of a fluorescence photon. Because of the Stokes shift, there is generally a red shift in the wavelength of the emitted photon in comparison to the excitation radiation; that is, it has a greater wavelength. Stokes shift makes it possible to separate the fluorescent radiation from the excitation radiation.

The fluorescent light is split off from the excitation radiation by suitable dichroic beam splitters in combination with blocking filters and is observed separately. This makes it possible to show individual cell parts that are dyed with different dyes. In principle, however, multiple parts of a preparation can also be dyed simultaneously with different dyes which bind in a specific manner (multiple fluorescence). Special dichroic beam splitters are used again to distinguish the fluorescence signals emitted by the individual dyes.

In addition to excitation of dye molecules with a high-energy photon (single-photon absorption), excitation with a plurality of lower-energy photons is also possible (FIG. 1b). The sum of energies of the single photons corresponds approximately to a multiple of the high-energy photon. This type of excitation of dyes is known as multiphoton absorption (Corle, Kino, "Confocal Scanning, Optical Microscopy and Related Imaging Systems"; Academic Press 1996). However, the dye emission is not influenced by this type of excitation, i.e., the emission spectrum undergoes a negative Stokes shift in multiphoton absorption; that is, it has a smaller wavelength compared to the excitation radiation. The separation of the excitation radiation from the emission radiation is carried out in the same way as in single-photon excitation.

The prior art will be explained more fully in the following by way of example with reference to a confocal laser scanning microscope (LSM) (FIG. 2).

An LSM is essentially composed of four modules: light source, scan module, detection unit, and microscope. These modules are described more fully in the following. In addition, reference is had to DE19702753A1.

Lasers with different wavelengths are used in an LSM for specific excitation of different dyes in a preparation. The choice of excitation of wavelength is governed by the absorption characteristics of the dyes to be examined. The excitation radiation is generated in the light source module. Various lasers (argon, argon/krypton, Sapphire lasers) are used for this purpose. Further, the selection of wavelengths and the adjustment of the intensity of the required excitation wavelength is carried out in the light source model, e.g., using an acousto-optic crystal. The laser radiation subsequently reaches the scan module via a fiber or a suitable mirror arrangement.

The laser radiation generated in the light source is focused in the preparation in a diffraction-limited manner by the objective through the scanner, scan optics and tube lens. The focus is moved in two dimensions in x-y direction over the specimen. The pixel dwell times when scanning over the specimen are mostly in the range of less than one microsecond to several seconds.

In confocal detection (descanned detection) of fluorescent light, the light emitted from the focal plane (specimen) and from the planes located above and below the latter reaches a dichroic beam splitter (MDB) via the scanner. This dichroic beam splitter separates the fluorescent light from the excitation light. The fluorescent light is subsequently focused on a diaphragm (confocal diaphragm/pinhole) located precisely in a plane conjugate to the focal plane. In this way, fluorescent light components outside of the focus are suppressed. The optical resolution of the microscope can be adjusted by varying the size of the diaphragm. Another dichroic blocking filter (EF) which again suppresses the excitation radiation is located behind the diaphragm. After passing the blocking filter, the fluorescent light is measured by a point detector (PMT).

When using multiphoton absorption, the excitation of the dye fluorescence is carried out in a small volume in which the excitation intensity is particularly high. This area is only negligibly larger than the detected area when using a confocal arrangement. Accordingly, a confocal diaphragm can be dispensed with and detection can be carried out directly following the objective (nondescanned detection).

In another arrangement for detecting a dye fluorescence excited by multiphoton absorption, descanned detection is carried out again, but this time the pupil of the objective is imaged in the detection unit (nonconfocal descanned detection).

From a three-dimensionally illuminated image, only the plane (optical section) coinciding with the focal plane of the objective is reproduced by both detection arrangements in connection with corresponding single-photon absorption or multiphoton absorption. By recording a plurality of optical sections in the x-y plane at different depths z of the specimen, a three-dimensional image of the specimen can be generated subsequently in computer-assisted manner.

Accordingly, the LSM is suitable for the examination of thick preparations. The excitation wavelengths are determined by the utilized dye with its specific absorption characteristics. Dichroic filters adapted to the emission characteristics of the dye ensure that only the fluorescent light emitted by the respective dye will be measured by the point detector.

Currently, in biomedical applications, a number of different cell regions are labeled simultaneously by different dyes (multifluorescence). In the prior art, the individual dyes can be detected separately based on different absorption characteristics or emission characteristics (spectra). For separate detection, an additional splitting of the fluorescent light of a plurality of dyes is carried out with the secondary beam splitters (DBS) and a separate detection of the individual dye emissions is carried out in various point detectors (PMT x).

Flow cytometers are used for examining and classifying cells and other particles. For this purpose, the cells are dissolved in a liquid and are pumped through a capillary. In order to examine the cells, a laser beam is focused in the capillary from the side. The cells are dyed with different dyes or fluorescing biomolecules. The excited fluorescent light and the backscattered excitation light are measured. The separation of the fluorescence signal of the specimen from the excitation light is carried out by means of dichroic beam splitters (MDB, see FIG. 2). The art is described in "Flow Cytometry and Sorting", second edition, M. R. Melamed, T. Lindmo, M. L. Mendelsohn, eds., Wiley & Sons, Inc., N.Y., 1990, 81-107.

The size of the cells can be determined from the backscattered signal. Different cells can be separated and/or sorted or counted separately by means of the spectral characteristics of the fluorescence of individual cells. The sorting of the cells is carried out with an electrostatic field in different capillaries. The results, that is, for example, the quantity of cells with dye A in comparison to cells with dye B, are often displayed in histograms. The through-flow rate is typically about 10-100 cm/s. Therefore, a highly sensitive detection is necessary. According to the prior art, a confocal detection is carried out in order to limit the detection volume.

According to the prior art, line scanners, as they are called, are also used instead of point scanners (Corle, Kino, "Confocal Scanning Optical Microscopy and Related Imaging Systems", Academic Press 1996). The basic construction essentially corresponds to that of an LSM according to FIG. 2. However, instead of a point focus, a line is imaged in the specimen and the specimen to be examined is scanned in only one direction (x or y). The image acquisition rate can be substantially increased by scanning a line instead of a point. Therefore, this scanning method can be used for observing high-speed processes in real time (real time microscopy). However, the optical axial resolution is reduced by a factor of approximately 1.4 compared with a point scanner.

In another arrangement for real time microscopy according to the prior art, the entire field to be examined is illuminated by an expanded light source. However, only special point patterns of the total field to be scanned are uncovered by a rapidly rotating disk. These methods are mostly known in technical literature as Nipkow disk methods (Corle, Kino, "Confocal Scanning, Optical Microscopy and Related Imaging Systems", Academic Press 1996).

In another method according to the prior art, known as structured illumination (see FIG. 3), the modulation depth of the optical imaging of an amplitude structure (e.g., grating) is used as a criterion for the depth of field. The image of the periodic structure is distinguished by the frequency of the modulation and the phase position (image phase) of the modulation. Various projection scenarios can be obtained by means of a phase shift of the structure at right angles to the optical axis. Generally, at least three phase images PB are required at 0°, 120° and 240° in order to calculate depth-discriminated optical sections without stripes. These phase images (PB) are subsequently calculated to form a (confocal) optical section image in an image processor by the following formula:

$$I_{Section}(x) = Const \cdot \sqrt{(I(x, 0°) - I(x, 120°))^2 + (I(x, 120°) - I(x, 240°))^2 + (I(x, 0°) - I(x, 240°))^2},$$

where I(x, angle) describes the intensity at the respective pixel in the corresponding phase image.

It is simplest to carry out the recording of three or more phase images sequentially. In this connection, it is assumed that the specimen is not moved during the measurement of the images. The section images or section stacks which are calculated from the phase images in this way can be displayed subsequently on a standard PC and monitor by means of 3-D evaluating software. The spatial resolution along the optical axis depends on the wavelength of the light, the numerical aperture of the objective and the modulation frequency.

For a detailed description of the calculation algorithm, reference is had to T. Wilson, et al., "Method of obtaining sectioning by using structured light in a conventional microscope", *Optics Letters* 22 (24), 1997.

Arrangements for screening dyes, for example, in so-called chip readers are similar in optical construction to laser scanning microscopes. However, they scan an appreciably larger image field for the investigation of macroscopic specimens, for example, screening of active ingredients on a biochip. The edge length of the scan fields amounts to about 10 mm. These scan fields can be achieved, e.g., by increasing the scan angle of the galvoscanner, by arranging the specimen in an intermediate image of the microscope arrangement, or by a special objective arrangement (macroobjective) which images the intermediate image on the specimen in magnified manner.

According to the prior art, the separation of the excitation light from the light emitted by the specimen is carried out by spectral separation using Stokes shift by restricting the numerical aperture of the optics used for specimen illumination and detection or by splitting into different polarization directions.

Special dichroic beam splitters are used for the spectral separation of the excitation light from the light emitted by the specimen. As is shown in FIG. 3a, these dichroic beam splitters are usually constructed in such a way that they reflect the excitation light as efficiently as possible and transmit the light emitted by the specimen as efficiently as possible. The reflection factor (reflectivity) is shown as a function of wavelength. When using polarized excitation light, the minimum spectral bandwidth (s) of the reflected wavelength range is about 10 nm; the edge steepness (f) is usually greater than 5 nm. Therefore, according to the prior art, the light emitted by the specimen can be efficiently separated with a dichroic beam splitter when using an excitation wavelength. However, efficiency decreases when a plurality of dyes with a plurality of wavelengths are excited simultaneously (multifluorescence microscopy), since a spectral overlapping of the excitation light and the emitted light usually occurs. Further, a special beam splitter must be created each time when using different dyes with different absorption characteristics. In a widefield microscope, there is usually a broadband excitation of the specimen with light from a white light source with partial spectral overlapping of the excitation radiation and emitted radiation. Accordingly, the use of dichroic beam splitters according to the prior art results in a poor efficiency of separation of excitation light and emitted light.

The separation of excitation light from emitted tight by restricting the numerical aperture of the specimen illumination optics (4 in FIG. 3b) can be carried out, for example, by illuminating the specimen with a restricted aperture, so that only the near-axis beams (1) travel in the direction of the specimen (2). Since the emission is carried out in all spatial directions, this light from the specimen (2) can be collected in the rest of the aperture area. The separation of the excitation light from the emitted light is carried out subsequently by a partially fully reflecting (black area) plane plate (3). The detection of the light emitted by the specimen is carried out in the radiating direction (5). The methods for dividing the numerical aperture known from the prior art (e.g., Pawley, Handbook of Confocal Microscopy, 1995) are disadvantageous in that the efficiency of detection and the optical resolution of the arrangement are worsened by the restriction of the aperture. These two parameters are connected in this regard. For example, a highly efficient separation is achieved at the expense of worsened optical resolution.

Problems of the Prior Art

In all of the methods according to the prior art, it is disadvantageous that the separation of the excitation light from the light emitted by the specimen is carried out in a wavelength-dependent manner, i.e., can not be adjusted in a flexible manner, or with a limited efficiency of typically 70% to 90%, depending on the required spectral characteristics and the quantity of illumination lines.

OBJECT AND SUMMARY OF THE INVENTION

The primary object of the invention is to overcome the stated problems of the prior art. The invention describes methods and arrangements by which the excitation light can be separated from the light radiation (e.g., fluorescence or luminescence) excited and/or backscattered in the specimen in a particularly advantageous manner with high efficiency. In contrast to the prior art, the separation is adjustable in a flexible manner as regards spectrum Without the movement of mechanical components and is therefore particularly suitable especially for use in multifluorescence microscopy, i.e., for simultaneous excitation of different dyes. In addition, the suppression of interference light is improved by at least an order of magnitude. Accordingly, fast switching between several excitation wavelengths or spectral detection wavelength ranges—so-called multitracking, as described in EP977069 A2—can be realized in a particularly simple manner. Further, it is possible to separate the light scattered by the specimen in the direction of the detector from the light reflected on a direct path and to measure it separately. In addition, a measurement of the polarization direction of the light coming from the specimen can be carried out. A further advantage consists in that fluctuations in laser output caused by unstable coupling into a glass fiber can be prevented by regulation, so that the output can be kept constant at the location of the specimen.

Unlike the arrangements for separating the excitation beam path from the detection beam path according to the prior art, optical resolution is not impaired by the arrangements according to the invention. Further, the illumination distribution can be manipulated at the site of specimen interaction. This makes it possible to scan so-called regions of interest (ROI) in real time. In addition, illumination methods known from widefield microscopy such as oblique illumination can be realized.

The solution according to the invention can be used in image-generating microscope systems as well as in analytic microscope systems. The microscope systems are image-generating systems such as laser scanning microscopes for three-dimensional examination of biological preparations with an optical resolution of up to 200 mn, nearfield scanning microscopes for high-resolution examination of surfaces with a resolution of up to 10 nm, fluorescence correlation microscopes for quantitative determination of molecular concentrations and for measuring molecular diffusions. Also included are methods based on fluorescence detection for screening dyes and methods for flow cytometry.

In all of the systems mentioned above, fluorescent dyes are used for specific labeling of the preparations. The above-stated objective is achieved by methods and arrangements according to the independent patent claims. Preferred further developments are indicated in the dependent claims.

The quantity of dye signatures that may be used simultaneously, i.e., the quantity of characteristics, for example, of cells that can be investigated simultaneously, can be increased by means of the methods according to the invention. When the spectral signatures of the individual dyes overlap extensively or are very close to one another, the detected wavelength range or numerical aperture must be limited, according to the prior art, for separate detection of the fluorescence signals of individual dyes. This reduces the sensitivity of detection, i.e., increases the noise of the detectors, because greater amplification must be used. This is avoided by the methods and arrangements according to the invention.

DESCRIPTION OF THE PREFERRED EMBODIMENTS

Figure 1:
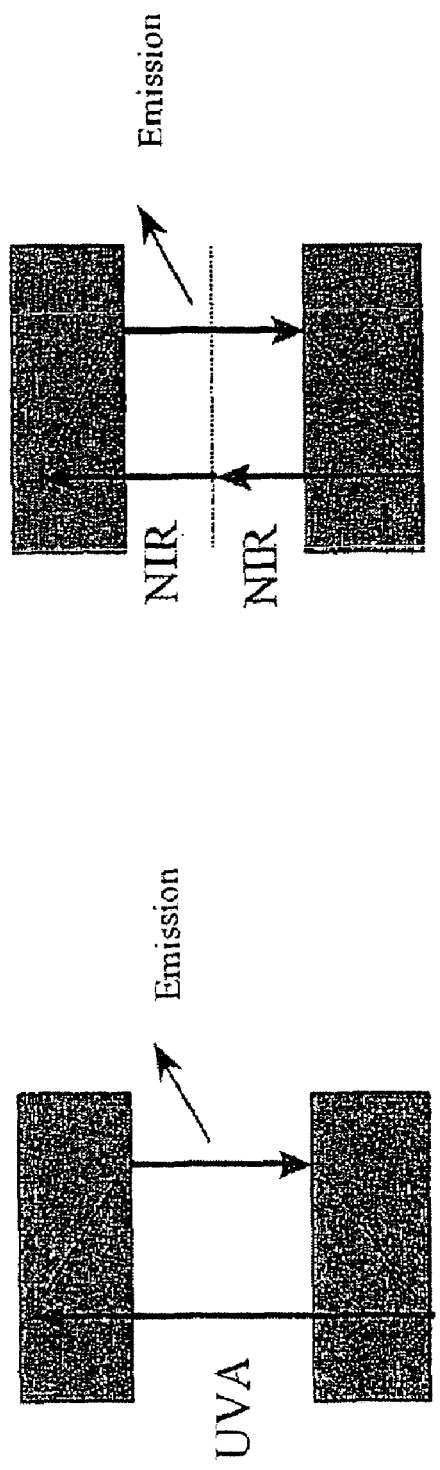
FIG. 1a is a representational drawing showing single photon absorption.
FIG. 1b is a representational drawing showing multiphoton absorption.
Figure 2:
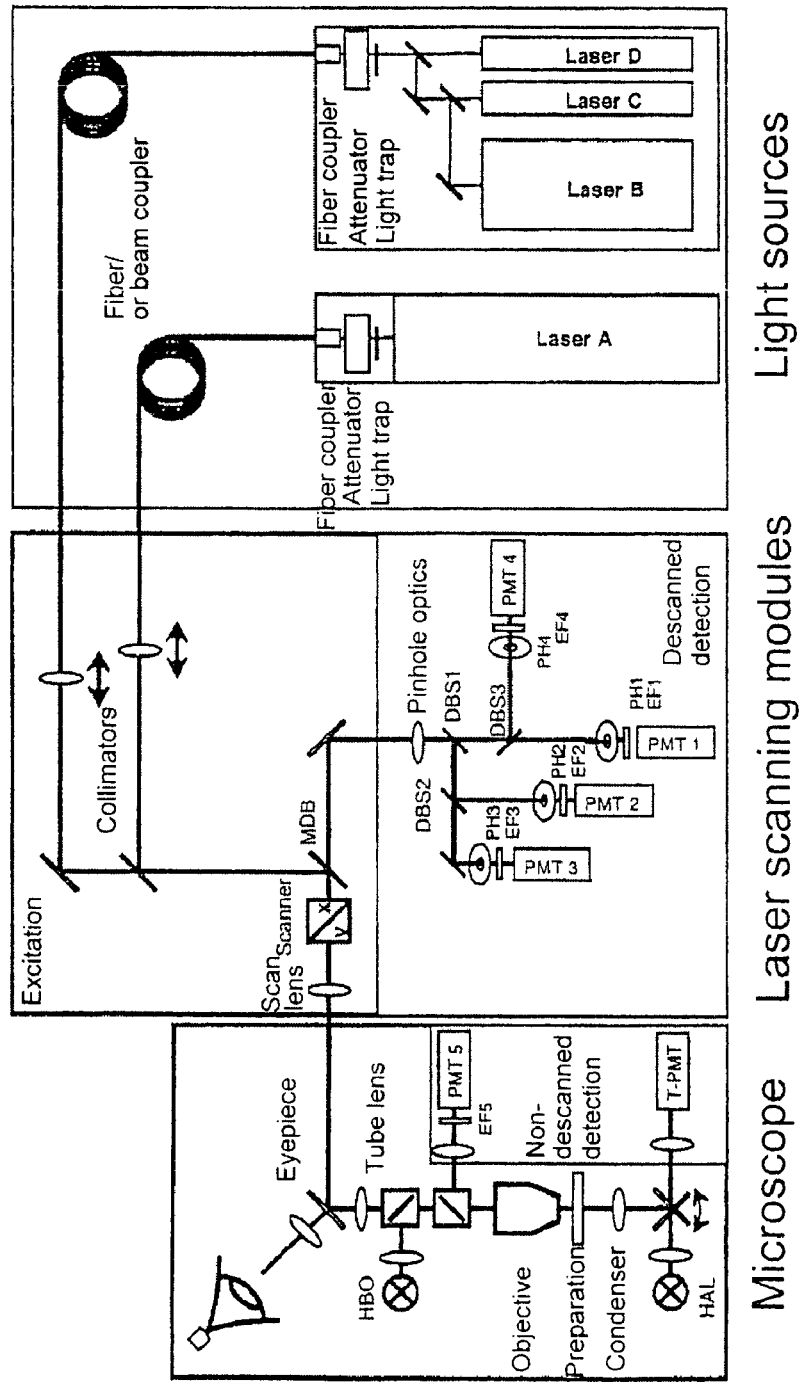
FIG. 2 is a block diagram of a laser scanning microscope.
Figure 3:
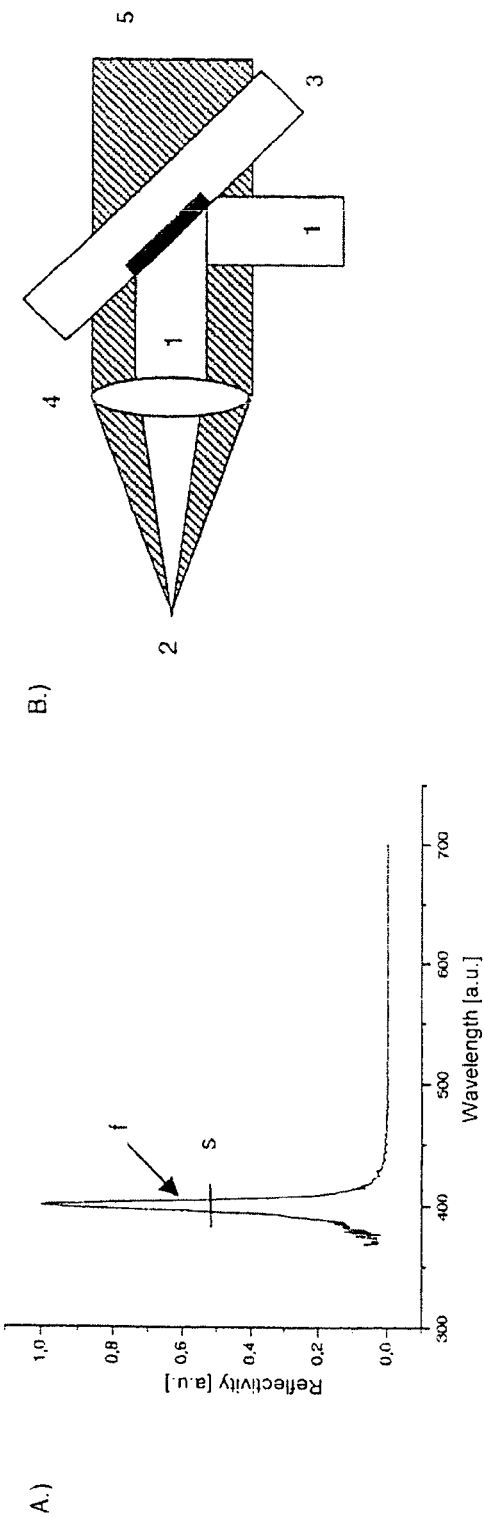
FIG. 3a is a graphical representation of the spectral separation of the excitation light from the light emitted by the specimen by the use of special diochroic beam splitters.
FIGS. 3b and 3c are cross-sectional representations of a splitter for separating excitation light from emitted light.

Various arrangements by which the light radiation (hereinafter, detection light) excited and/or backscattered in the specimen can be separated from the excitation light in a particularly efficient manner will be described more fully in the following. The arrangements are accordingly suitable in particular for fast multitracking with a flexible separation of the excitation radiation from the detection light that is adapted with respect to spectrum. In the following context, light that is emitted by the specimen is light which is preferably radiated from the specimen in a large solid angle. This light is not polarized (unpolarized). This refers in particular to fluorescent light and luminescent light excited in the specimen and backscattered light.

1. Principle of operation of the arrangement for variable separation of excitation light from detection light The construction of the arrangement for separating the excitation light from the detection light is shown schematically in FIG. 4 for the detection beam path and in FIG. 5 for the excitation beam path. The arrangement substantially comprises at least three polarizing beam splitter cubes P1 to P3. P4 can be another polarizing beam splitter cube or a mirror. Glan laser polarization splitters, birefringent materials or beam splitters with special microstructures (e.g., MicroWires by Moxtek, Inc., Orem, USA), for example, can be used as polarizing beam splitter cubes. Two dispersive elements (e.g. prisms or gratings) D1 and D2 which spatially split the light radiation spectrally along the Y-coordinate and then recombine (see also FIG. 6) are arranged between every two beam splitter cubes (P2 and P1; P4 and P3). Optics L1 and L2 are located at a distance from their respective focal length f, which can also differ for the optics, between the dispersive elements D1 and D2 and an element for rotating polarization, for example, a spatial light modulator (SLM) S. The optics L1 and L2, together with the dispersive elements D1 and D2, serve to generate a spectral Fourier plane at the location of the SLM S. In this plane, the spectral components of the light coming from direction 2 or direction 1 are separated spatially along the y-coordinate. The SLM (e.g., SLM640 by Jenoptik, Germany) comprises a series of strips (there are 640 strips in the SLM 640) which can be controlled individually. The polarization direction of the light passing through can be varied depending on the control of the respective pixel. SLMs are used in the art in pulse shapers (Stobrawa, et al., *Apl. Phy.* B72, 627-630 (2002)). In this case, a phase delay and/or a change in amplitude of the spectral components of the light source are/is carried out through the action of the SLM in combination with dispersive elements. In contrast to the arrangements described in the following, the light source must be linearly polarized for this purpose because, otherwise, energy loss would occur. Instead of an SLM, a plurality of adjustable half-wave plates arranged in the Fourier plane can also be used, for example.

Figure 5:
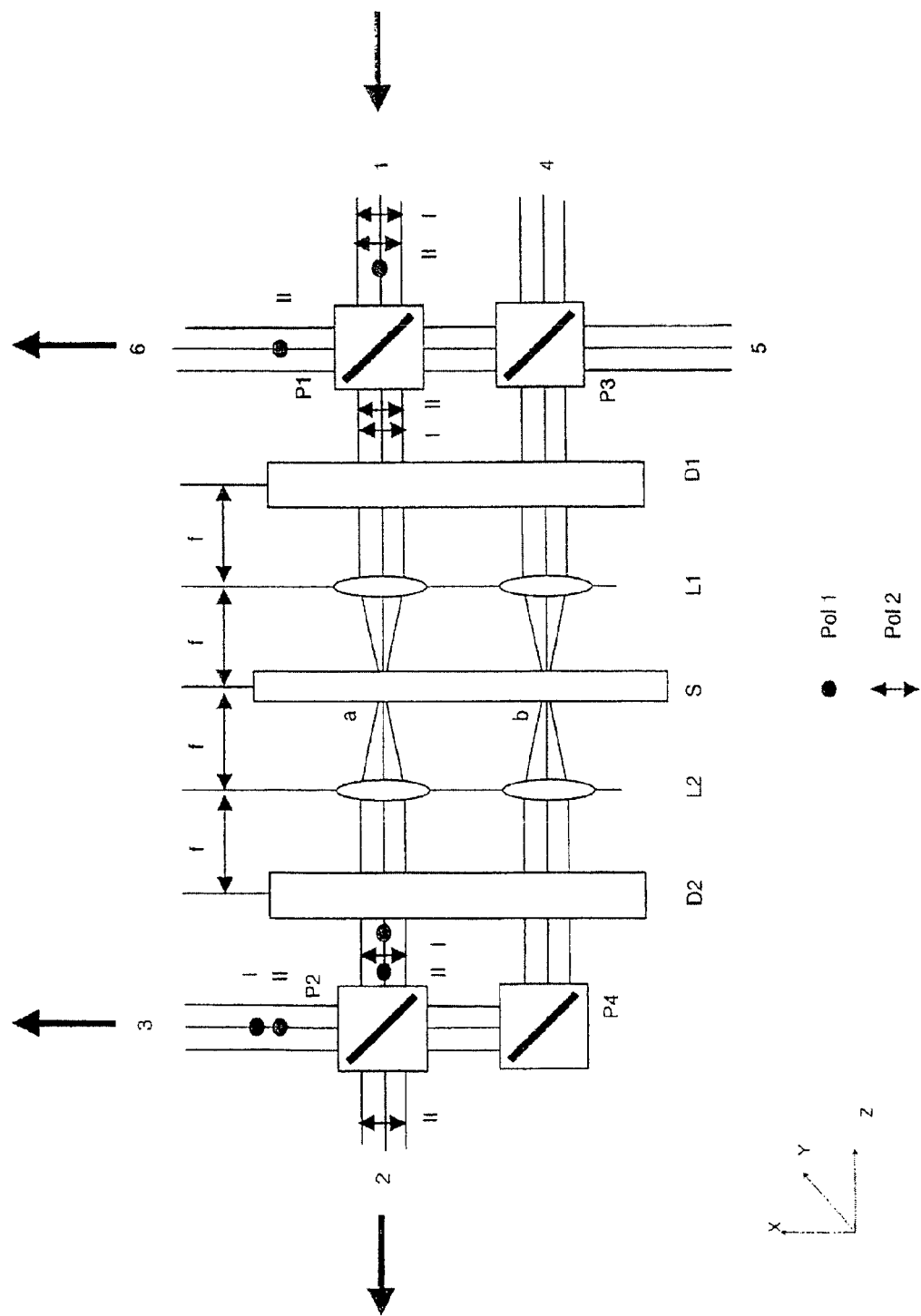
FIG. 5 illustrates in schematic representation an arrangement in accordance with the invention for separating excitation light from the detection light for the excitation beam path.
Figure 6:
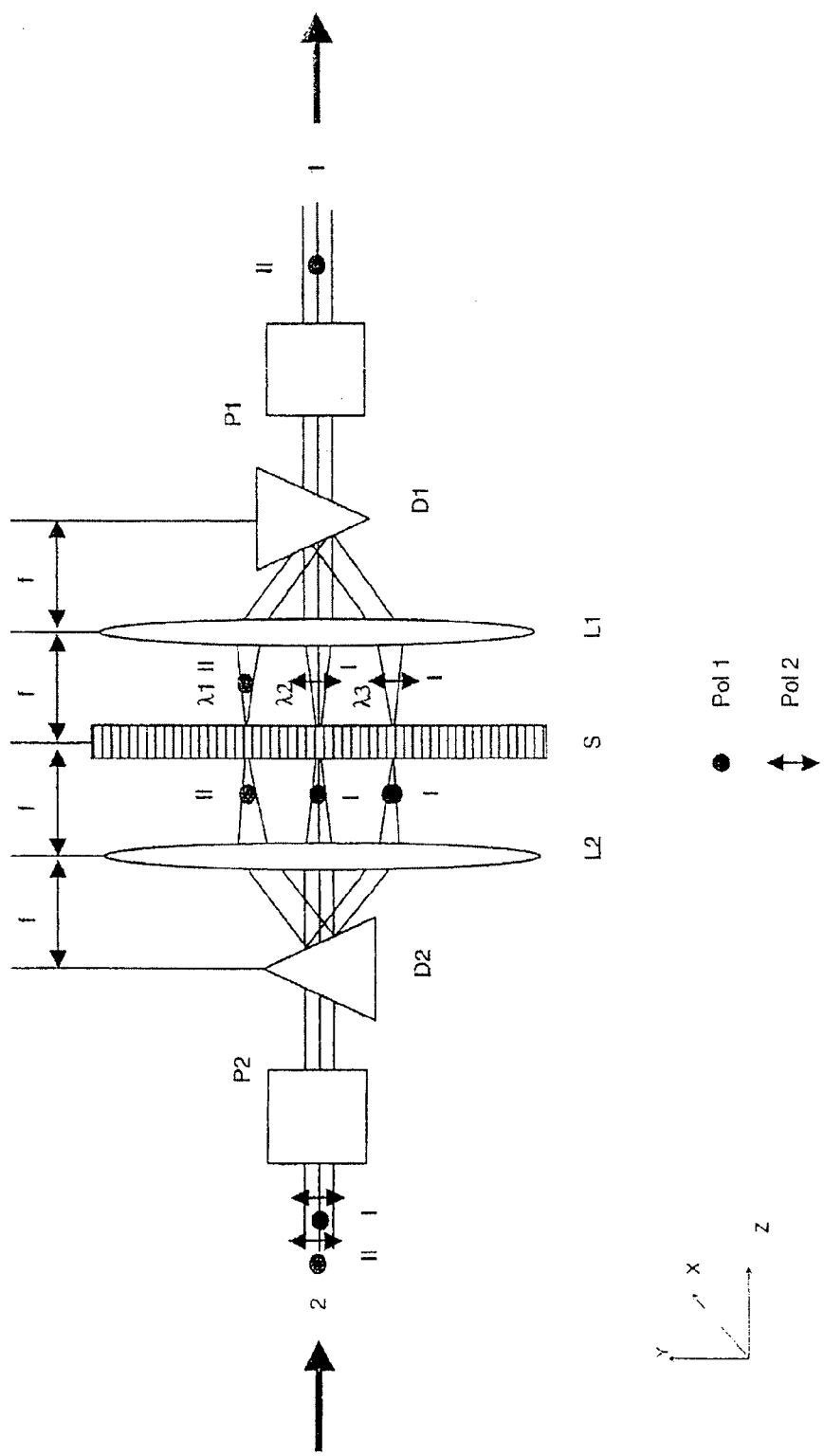
FIG. 6 shows, in schematic form, the arrangement from FIGS. 4 and 5 in the yz plane in which the spectral splitting of the light is carried out due to the action of the dispersive element.
Figure 7:
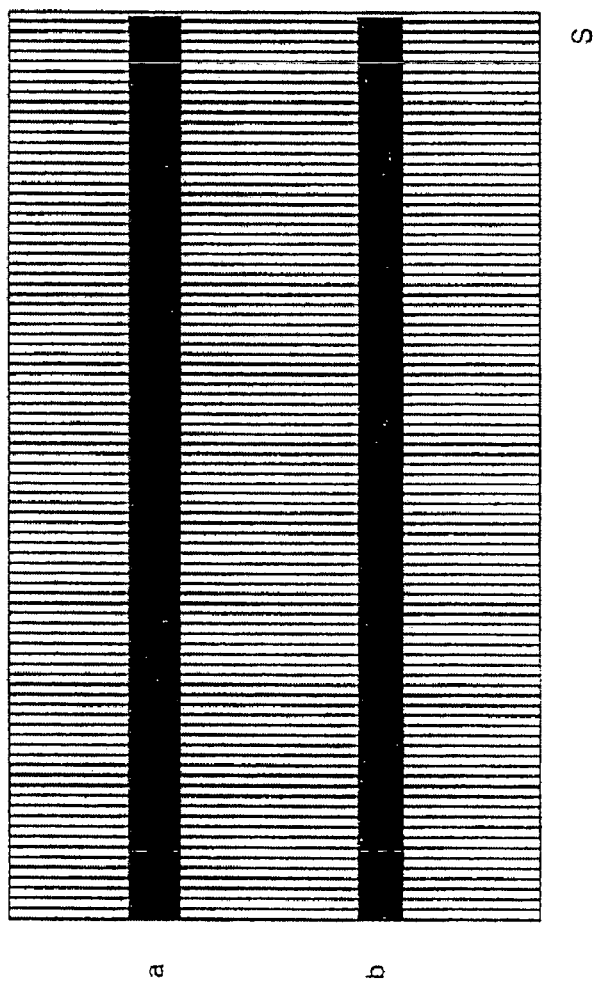
FIG. 7 shows the SLM S in the xy-plane.

The SLM is traversed in areas a and b (see FIGS. 4, 5, 7), wherein the strips are oriented along the x-axis. FIG. 6 shows the arrangement from FIGS. 4 and 5 in the yz-plane in which the spectral splitting of the light radiation is carried out due to the action of the dispersive elements D1 and D2. Due to the spatial separation of the individual spectral components of the light radiation, the latter passes through different pixels of the SLM S. FIG. 7 shows the SLM S in the xy-plane. The individual pixels (strips) can be seen along the y-axis. The spectral splitting of the light radiation by the dispersive elements D1 and D2 is carried out along this axis. The black strips along the y-axis show areas a and b through which the different polarization directions Pol1 and Pol2 pass.

Figure 4:
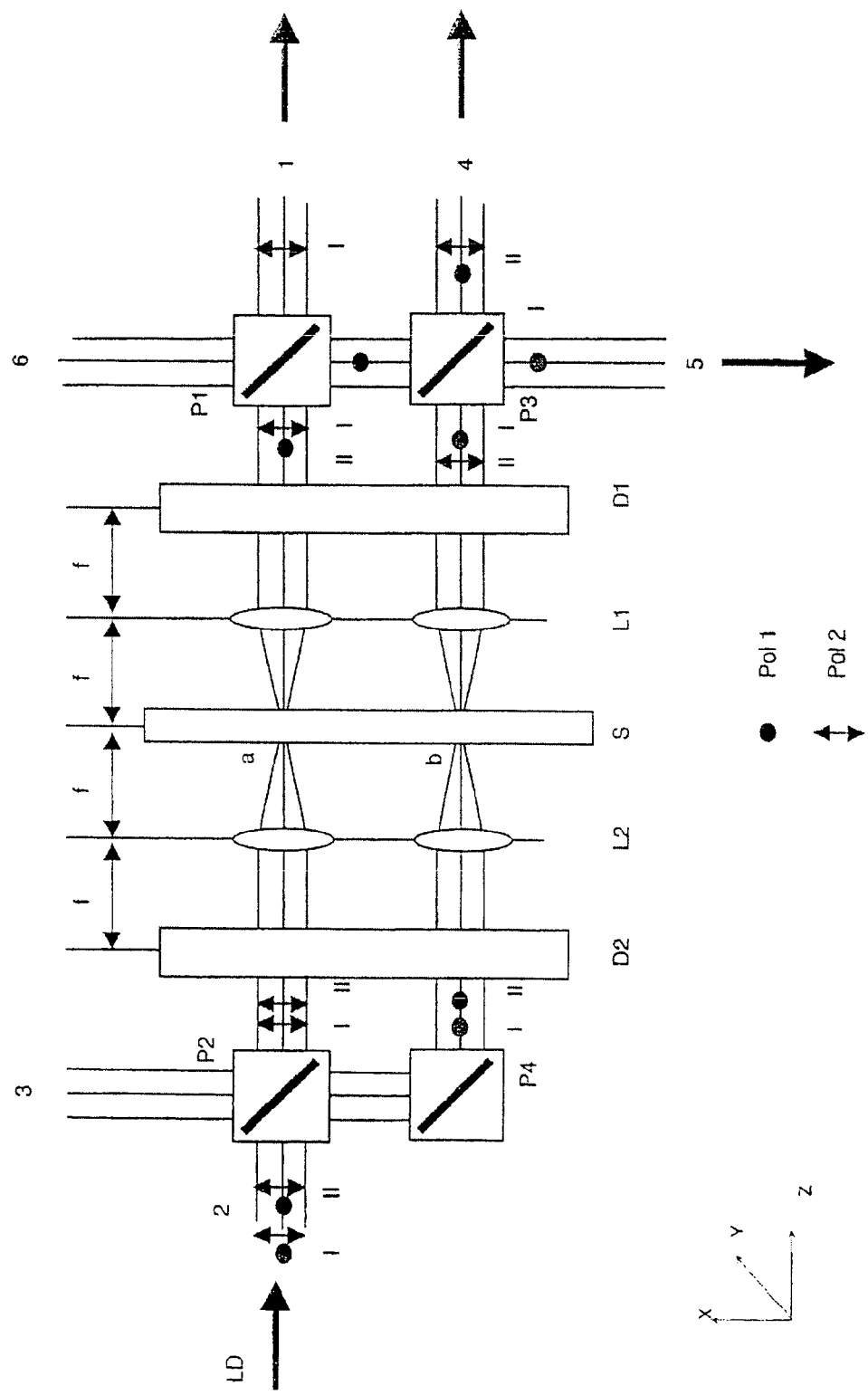
FIG. 4 illustrates in schematic representation an arrangement in accordance with the invention for separating excitation light from the detection light for the detection beam path.

The principle of operation will be explained in the following with reference to FIG. 4 for the detection beam path. Unpolarized light LD which is coupled in in the direction indicated by the arrow (2) is split at pole splitter P2 into two polarization components Pol1 which are reflected perpendicular to one another (circles, pole direction in the viewing direction) and continuous polarization components Pol2 (arrows, pole direction in the direction of the arrow). The gray (II) and black (I) symbols represent light of different wavelengths (e.g., black (I) is fluorescence and gray (II) is scattered excitation light). Pol1 of different wavelengths (λ1, λ2, λ3) travels from P2 via P4 and Pol2 travels from P2 directly through D2 and L2 to different regions of the SLM S (see FIG. 6), namely, Pol 1 to region b and Pol 2 to region a (see also FIG. 7). The SLM rotates, for example, the polarization for the light radiation (shown in black (I)) falling on areas λ2 and λ3, e.g., by exactly 90° (FIG. 4). The spatial separation of the spectral components through L1 and D1 is then canceled and the light travels to pole splitters P1 and P3, wherein the gray (II) and black (I) components (i.e., the fluorescent radiation and the excitation radiation in the present example) are polarized perpendicular to one another in the two arms or branches P2-P1 and P4-P2, respectively (FIG. 4). The excitation light (gray (II) components) accordingly exits through the coupling ports 1 and 5. The two polarization directions of the fluorescent light (black (I) components) exit together through coupling port 4.

By means of the arrangement, light radiation entering through the input 2 can accordingly be spatially separated in the different outputs 1, 5 and 4 independent from the polarization state due to their different spectral composition and can accordingly be further processed optically separately.

A rotation of the polarization by angles other than 90 degrees in the detection beam path for fluorescence measurement is possible, but is less advisable because the components of the fluorescent light then reach the coupling ports 1 and 5 also and are therefore not detected by a detector.

The principle of operation in the excitation beam path is effected in a corresponding manner and will be described with reference to FIG. 5. Unpolarized light passing through input 1 (arrow) is divided at P1 into two perpendicular polarization components Pol1 and Pol2. The gray (II) and black (I) symbols again represent light of different wavelengths (e.g., black excitation light of wavelength λ1 and red excitation light of wavelength λ2). Pol1 reaches output 6 directly. Pol2 of different wavelengths (λ1, λ2) travels from P1 via D1 and L1 to different regions of the SLM S (see FIG. 6). The SLM rotates the polarization for the light radiation (shown in black) impinging on area λ2 by exactly 90°, for example (FIG. 5). For wavelength λ1, the SLM rotates the wavelength by an angle not equal to 90° (preferably in the range of 0° to 180°), for example.

The spatial separation of the spectral components through L2 and D2 is canceled again subsequently and the light travels to P2. P2 separates the components, according to polarization, into the output 3 and output 2, respectively. In the example above, the polarization for wavelength λ2 is rotated by exactly 90° through the SLM. Therefore, all light of this wavelength is directed into output 3 through P2. In contrast, the polarization for wavelength λ1 is only rotated by an angle not equal to 90°. Therefore, the light output is split in the two outputs 2 and 3. The splitting ratio is given by the adjusted angle of rotation of the polarization at the SLM. A rotation of the polarization by angles not equal to 90 degrees in the excitation beam path is suitable for attenuating the excitation light, since the ratio of output in the coupling ports 2 and 3 can be adjusted continuously corresponding to the following equation: $P_2/P_3$=tan (angle of rotation).

Accordingly, by means of the arrangement, light radiation entering through input 1 can be spatially separated in the different outputs 2, 3 and 6 independent from the degree of polarization due to its different spectral composition and can accordingly be separately further processed optically.

2. Laser scanning microscope

Figure 8:
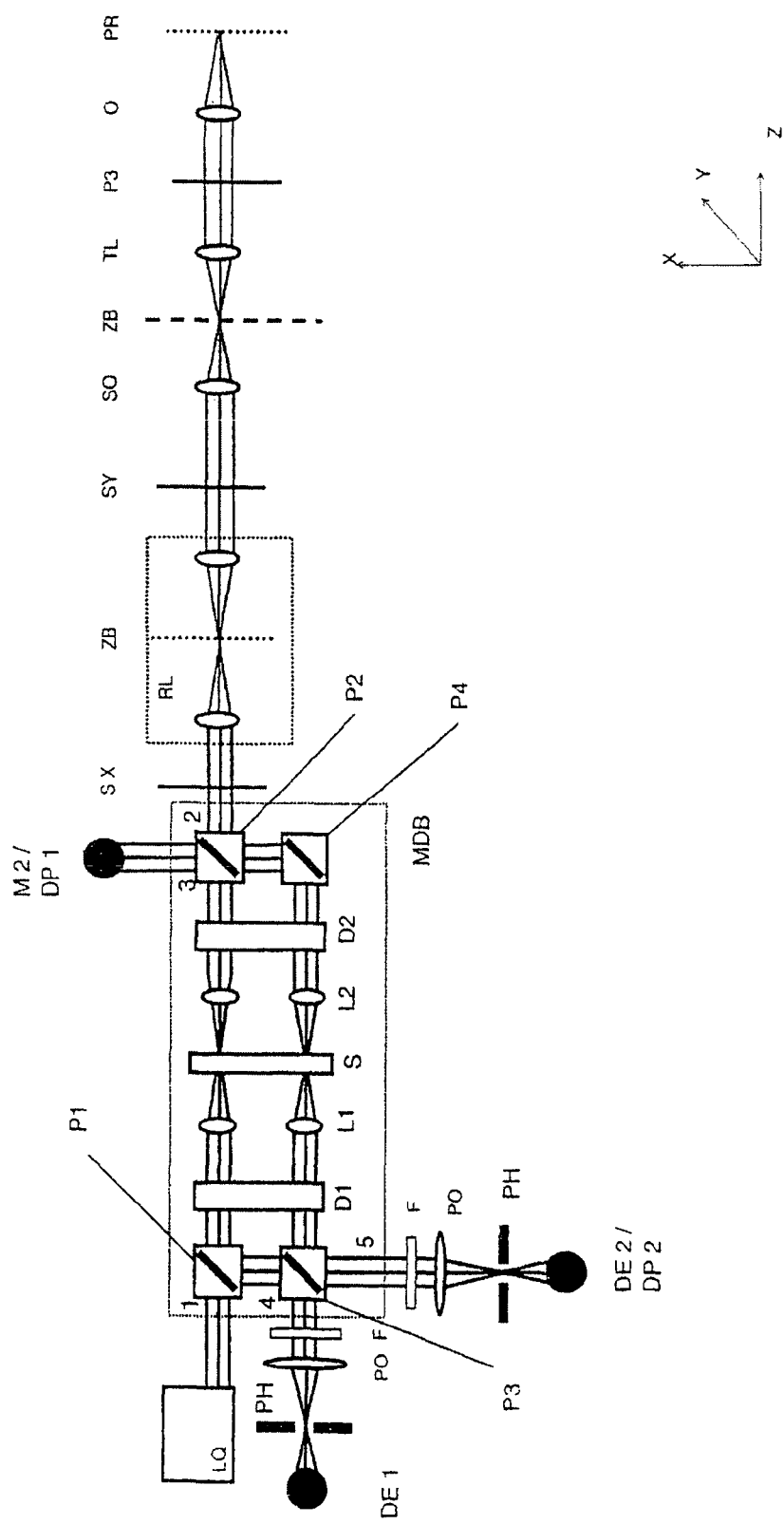
FIG. 8 shows, in schematic form, an arrangement of an MDB for separating illumination light and specimen light for a laser scanning microscope.

The arrangement according to the invention of an MDB (main color splitter) for separating illumination light and specimen light for a laser scanning microscope (LSM) in the xz-plane is shown schematically in FIG. 8. The principle of operation described in 1) with reference to FIGS. 4 to 7 can be used in an analogous manner in a microscope for flexible separation of the fluorescent radiation from the excitation radiation. In an LSM, the specimen is illuminated by a point focus which is displaced in the xy-plane by means of scanners SX and SY. For this purpose, the preferably linearly polarized light source LQ is coupled into the MDB (see FIGS. 5 and 6) via port 1 in P1. The light of the light source LQ then passes through the dispersive element D1 and the optics L1 preferably to one pixel (area a) of the SLM S. If the excitation light is to reach the specimen, the corresponding pixels are not controlled, i.e., the polarization direction of the light is not changed and the excitation light arrives at the output 2 of the MDB. When the above-mentioned pixels (area a) of the SLM are controlled, the polarization direction of the excitation light is rotated and, depending on the polarization direction, a portion of the light accordingly reaches output 2 and the remaining component arrives at output 3. A monitor diode M2 for determining the excitation light output which can serve as a regulating quantity for compensation of intensity fluctuations caused by coupling in different polarization directions, e.g., of a glass fiber, is located at output 3. Further, this type of operation can also be used for fast switching off or attenuation of individual wavelengths of the light source.

The linearly polarized excitation light coupled in the direction of output 2 (see FIG. 5) reaches the scanners SX and SY which are located in a pupil plane of the microscope arrangement conjugate to the back focal plane of the objective (P3), so that the scanners can move the excitation point in the xy plane of the specimen, i.e., can scan the specimen, this excitation point being focused in a diffraction-limited manner. The imaging in the specimen is carried out by means of the scanning optics (SO), the tube lens (TL) and the objective (O). The relay optics (RL) generate the conjugate pupil planes SX and SY of the microscope arrangement. In special arrangements according to the prior art, the relay optics can also be dispensed with. For example, they can be omitted when the distance between SX and SY is reduced.

The light emitted by the specimen is collected through optics O (e.g., a microscope objective) and is imaged together with the tube lens TL in an intermediate image plane ZB of the microscope arrangement. It travels from the latter location via the scanners SX/SY and the relay optics RL to the input 2 of the MDB again. Since the light emitted by the specimen is usually unpolarized, it is divided at the beam splitter P2 (see also FIG. 4) into two polarization directions Pol1 and Pol2 that are perpendicular to one another. When fluorescent light is excited in the specimen, for example, the spectrums of light is shifted relative to the excitation light due to Stokes shift. Through the action of the dispersive elements D1 and D2, the fluorescent light accordingly reaches pixels (area b) of the SLM that are not identical to the pixels of area a (see also FIG. 6). The pixels of area b are controlled in such a way that the polarization is preferably rotated by 90° relative to the incident light. The fluorescent light accordingly reaches output 4 (see FIG. 4). But the backscattered, unpolarized excitation light arrives at output 5 because it falls on the pixels of area a and the polarization is therefore not rotated.

Subsequently, the light of the specimen which travels through output 4 of the MDB by means of imaging optics (PO) is focused through a confocal diaphragm (PH), so that detection light which is outside of the focus is suppressed. In nonconfocal detection, the diaphragm can be omitted. A detector (DE1) which detects the light radiation excited in the specimen is located behind the confocal diaphragm. When recording fluorescence or luminescence, an emission filter (dichroic filter) F can be swiveled in for additional suppression of the excitation light backscattered from the specimen or for limiting the spectral detection area.

When the polarization of the emitted light of the specimen is to be detected (e.g., when determining fluorescence anisotropy), this can be carried out by detectors DE1 and DE2. The respective polarization can be composed from two portions or components which are polarized perpendicular to one another. The two portions which are polarized perpendicular to one another are measured separately by DE1 and DE2, e.g., by switching on a half-wave plate, not shown, between P1 and P3. The respective polarization can then be calculated by taking the ratio of the signals of detectors DE1 and DE2. Another method consists in controlling the corresponding SLM pixels in such a way that the signal is equal in both detectors DE1 and DE2. The corresponding polarization direction of the fluorescent light can then be determined from the control characteristic of the SLM pixel. A spectrally resolved measurement of fluorescence anisotropy is made possible in this way in that the pixels of the SLM are adapted sequentially for the individual colors.

The backscattered or reflected excitation light of the specimen which travels through the output 5 of the MDB (one portion travels in the direction of the light source LQ and is masked out) can also be focused through a confocal diaphragm (PH) by means of imaging optics (PO), so that detection light which lies outside of the focus is suppressed. A detector which detects excitation light that is backscattered from the specimen is located behind the confocal diaphragm.

Figure 9:
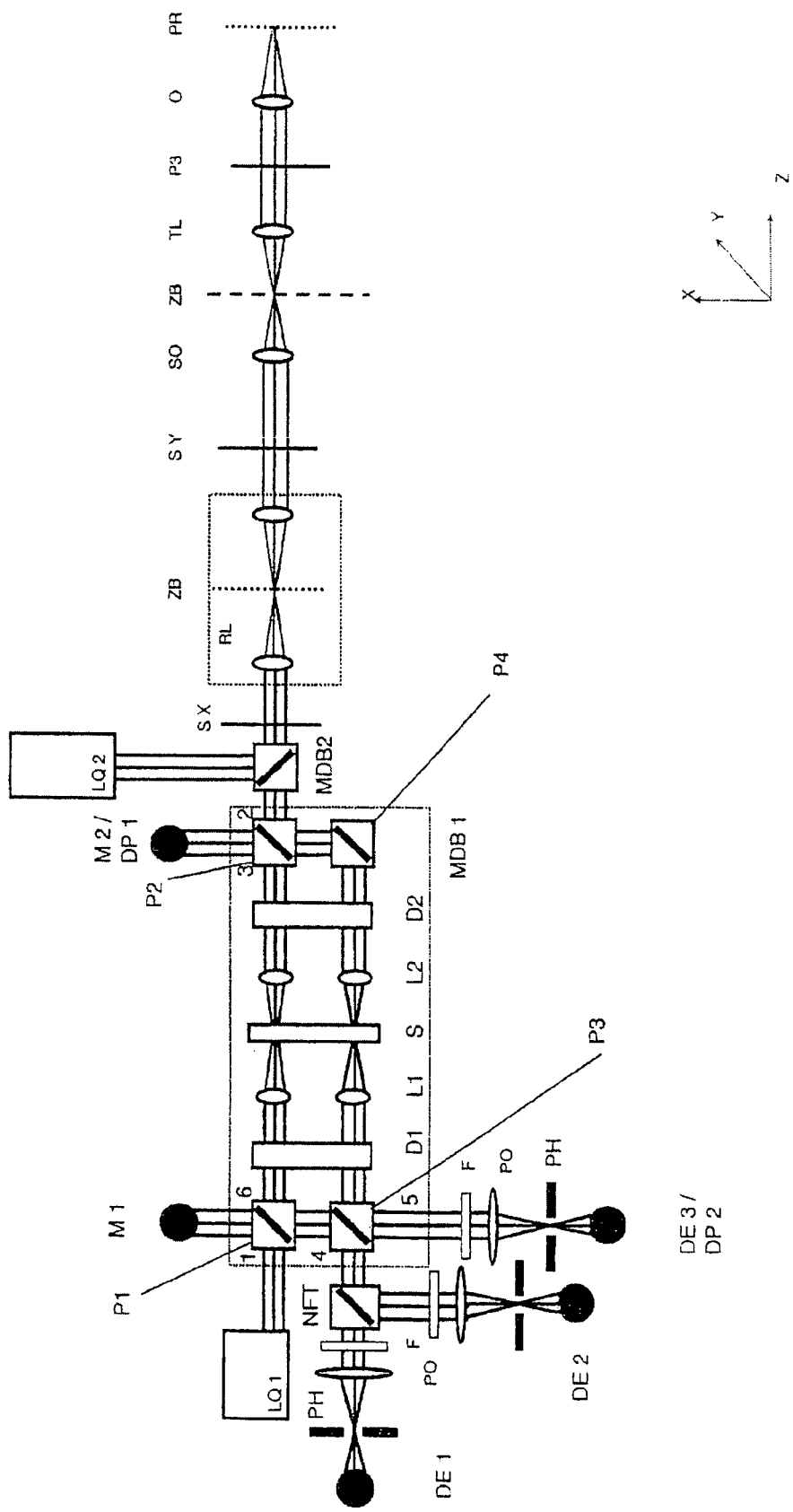
FIG. 9 shows another arrangement for a laser scanning microscope in accordance with the invention.

FIG. 9 shows schematically another construction of the arrangement according to the invention for a laser scanning microscope (LSM) in the xz-plane in which another light source LQ2 not running through the MDB1 is coupled. In addition to the arrangement already discussed with reference to FIG. 8, another monitor diode M1 is located at output 6 (see also FIG. 5). When the excitation radiation is coupled not only in polarization direction Pol1 but also in polarization direction Pol 2, M1 measures the coupled output. When the measurement signal M1 deviates from a reference value, the SLM can be controlled correspondingly in such a way that another corresponding reference value is adjusted at M2. Fluctuations in the coupling efficiency, e.g., in a glass fiber located between the light source LQ and the input 1 of the MDB, can be compensated by this regulation. The coupling efficiency and accordingly the light output coupled in the direction of the specimen can be influenced, for example, by de-adjusting the in-coupling into the glass fiber or by coupling in different polarization directions with the polarization-preserving glass fiber.

Many different types of light sources from a broad spectral range are currently used in fluorescence microscopy. Due to a lower transmission of the SLM in certain wavelength ranges, e.g., in UV light sources (less than 400 nm) or with multiphoton excitation (greater than 800 nm), the coupling of the light sources through the SLM is not desirable. These light sources (LQ2) can be combined correspondingly with the light sources LQ1 passing through the SLM by a conventional beam splitter MDB2 between the output 2 and the first scanner, e.g., SX. In these light sources, detection is usually carried out in the wavelength range between 400 and 800 nm, that is, for example, through the SLM or by detectors according to the prior art.

The light emitted by the specimen which strikes output 4 of the MDB 1 can also be split by dichroic beam splitters NFT according to the prior art onto different confocal detectors (e.g., DE1 and DE2).

Figure 11:
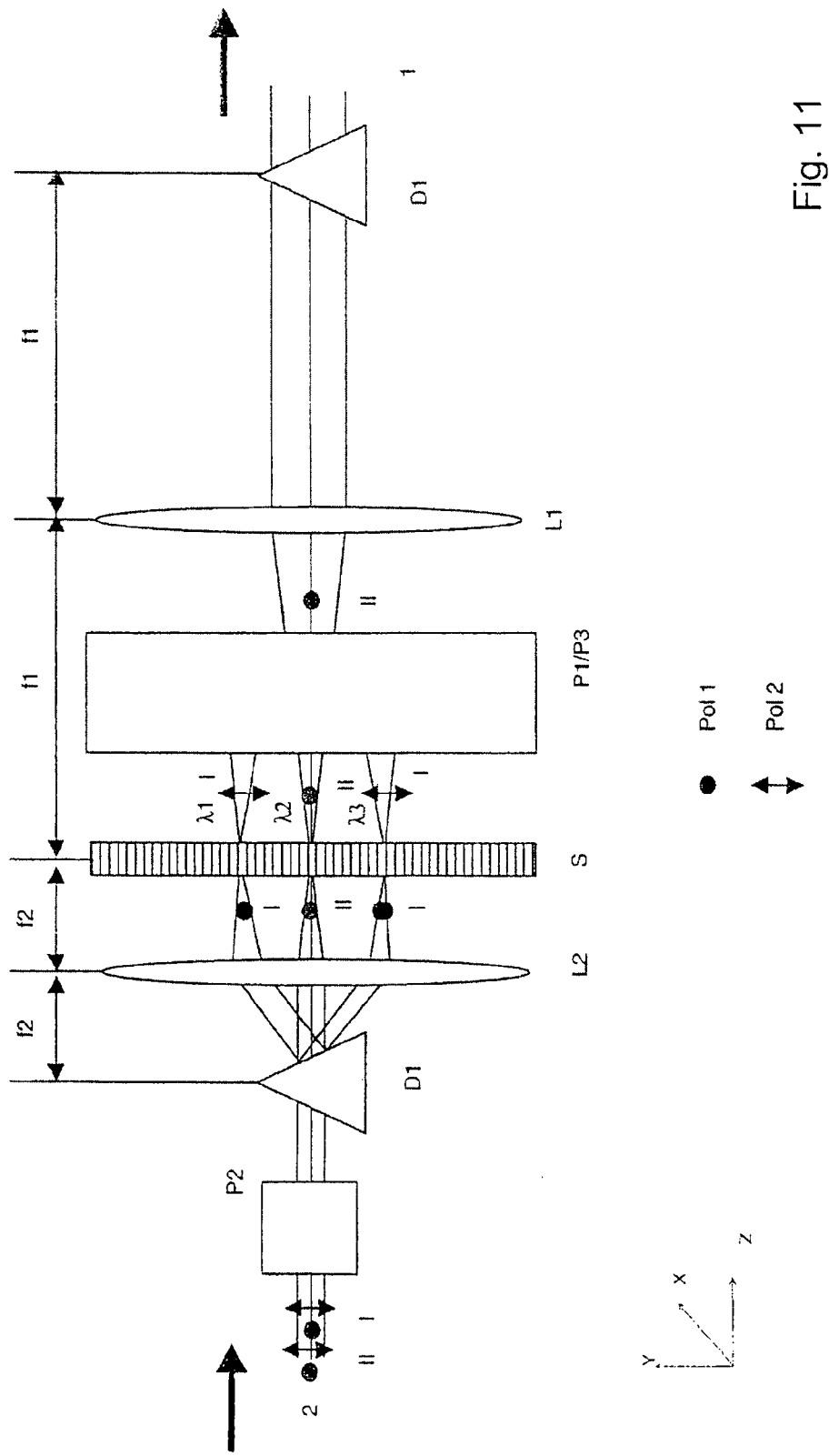
FIGS. 11 and 12 show yet another arrangement of a laser microscope in the yz plane and xz plane, respectively.
Figure 12:
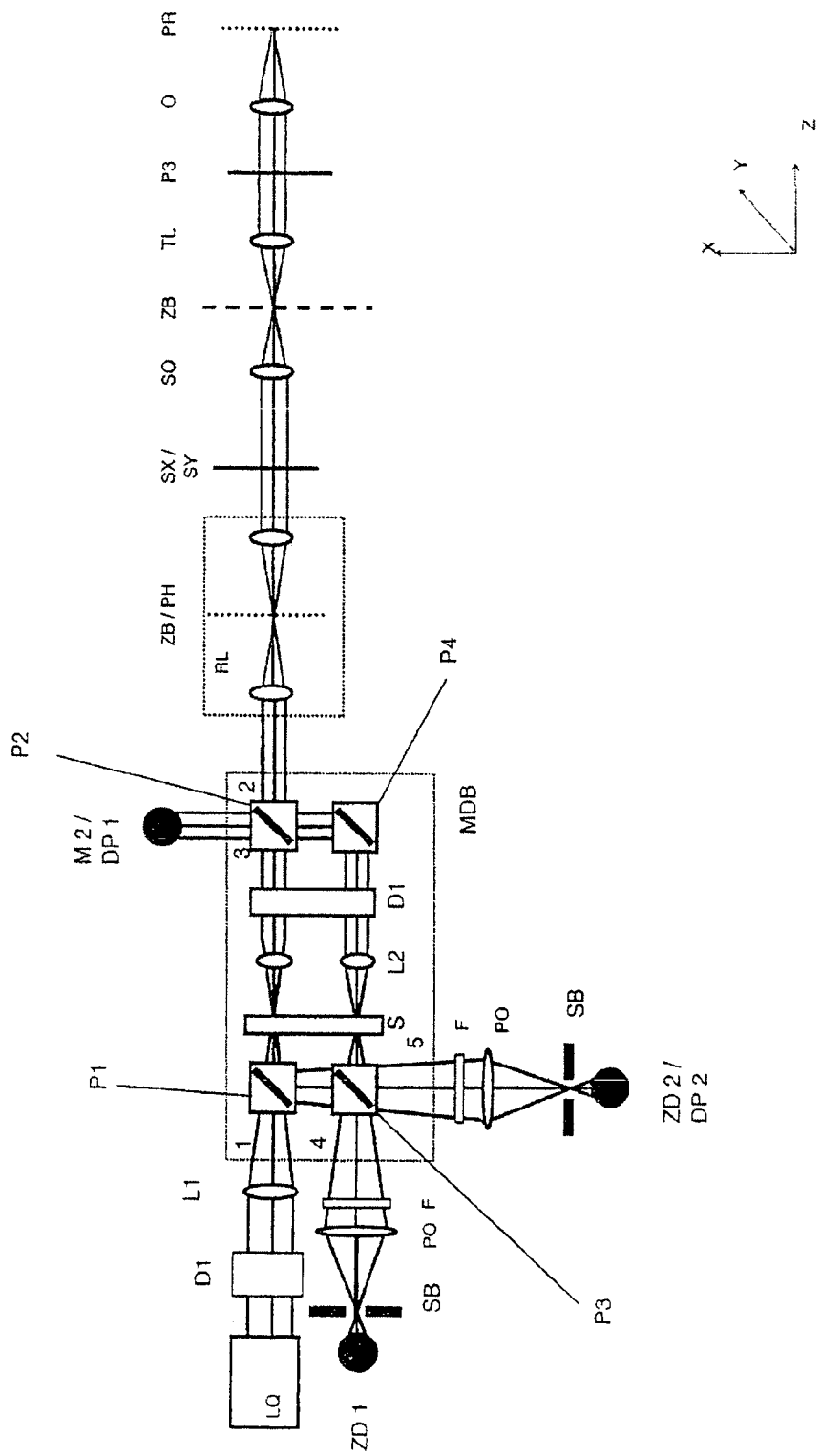

FIGS. 11 and 12 show another arrangement according to the invention in a laser scanning microscope in the yz-plane and in the xz-plane. The components act in a manner corresponding to the components described above. The modifications described in the following relate to the detection beam path. In this case, in contrast to the arrangements mentioned above, the light radiation to be detected from the specimen after traversing P2, P4, after spectral separation through D1 and manipulation of the polarization components in S through the beam splitters P1 and P3 (hidden behind P1 in the drawing) is separated from the excitation radiation. As is shown, P1 and P3 are extended along the Y axis in this case, so that the entire spectral distribution can be deflected through them. There is no recombination of the individual spectral components for the light radiation to be detected. Instead, there is a spectrally resolved measurement of the detection light which has a different polarization at P1 than the excitation light and, therefore, travels in the direction of detection with a line detector ZD1 for fluorescence or ZD2 for scattered light which is arranged in its longitudinal direction along the y-coordinate as is shown in FIG. 12. The imaging on the line detector is carried out through pinhole optics PO through a confocal slit diaphragm for adjusting the optical resolution. Instead of or in addition to the slit diaphragm, a pinhole diaphragm can also be arranged in the intermediate image PH/ZB. The confocal diaphragm PH can also be carried out in an intermediate image ZB/PH between the scanners SX/SY and the MDB by adding additional relay optics RL. This results in increased resolution because a pinhole diaphragm can be used instead of a slit diaphragm.

By means of this arrangement, a spectrally resolved measurement of the polarization characteristics can be carried out in a particularly advantageous manner corresponding to the method described above.

Outputs can also be exchanged in a corresponding manner in all of the arrangements according to the invention.

Figure 10:
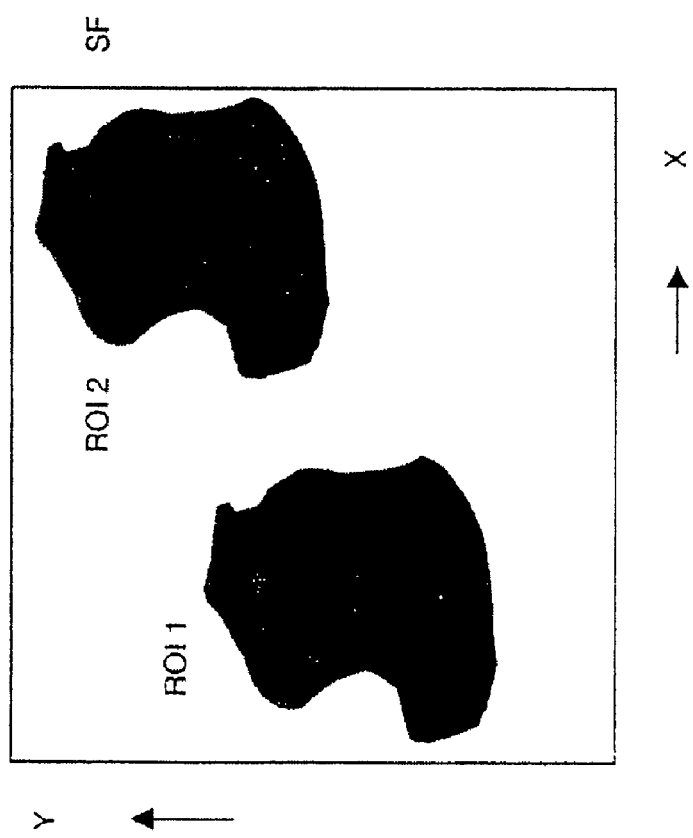
FIG. 10 shows, in graphical representation, two regions of spectral interest within the scan field.

The MDB shown in FIGS. 4 to 7 is also suitable for scanning regions of special interest ROI (see EP977069A2) (see FIG. 10). In this case, the laser light of a determined wavelength and output is released only for determined regions that are preselected by the user. FIG. 10 shows two regions ROI1 and ROI2 within the scan field by way of example. The wavelength is changed or the excitation output is adjusted by corresponding control of the SLM, resulting in a corresponding change in the polarization state.

In principle, the function of the scanner shown herein can also be taken over by a corresponding scan table (object scanner).

The invention is used in a particularly advantageous manner in a widefield microscope, a fluorescence microscope, a point-scanning laser scanning microscope or a line-scanning laser scanning microscope, a flow cytometer, a parallel confocal microscope with a pinhole array in the illumination beam path and/or detection beam path, or in a microscope arrangement for forming a periodic structure on an object with a phase displacement of the structure and the recording of phase-shifted images of the object.

While the foregoing description and drawings represent the present invention, it will be obvious to those skilled in the art that various changes may be made therein without departing from the true spirit and scope of the present invention.

What is claimed is:

1. In a microscope arrangement, a method for changing a spectral composition or intensity of illumination light or specimen light, comprising the steps of:

positioning a specimen in a microscope;

carrying out a spatial separation into radiation components of different polarization with a first polarizing device;

carrying out a spectral, spatial splitting of at least one radiation component of different polarizations with a first dispersion device;

changing the polarization state of at least one part of the spectrally spatially split radiation component; and carrying out a spatial separation or a combination of radiation components of different polarization by a second polarizing device wherein carrying out a spatial separation into radiation components of different polarizations with a first polarizing device or combining the radiation components of different polarization by a second polarizing device is adjustable in flexible manner without the movement of mechanical components.

2. The method according to claim 1, wherein radiation components which are changed with respect to their polarization state and radiation components which are unchanged with respect to their polarization state are spatially united by a second dispersion device.

3. The method according to claim 1, including the step of performing a measurement in parallel or sequentially for detecting a polarization state of a detection light.

4. A method according to claim 1, including the step of compensating fluctuations in intensity in an excitation light brought about by a light source or optical elements.

5. An optical arrangement in a microscope for changing the spectral composition or intensity of illumination light comprising:
   a light source provided in the microscope;
   a first polarizing device for spatial separation into radiation components of different polarization;
   a first dispersion device for spectral spatial splitting of at least one radiation component which are arranged before or after said first polarizing device;
   a means for changing the polarization state of at least one part of the spectrally spatially split radiation component; and
   a second polarizing device for the spatial separation or combination of radiation components of different polarization
   wherein carrying out a spatial separation into radiation components of different polarizations with a first polarizing device or combining the radiation components of different polarization by a second polarizing device is adjustable in flexible manner without the movement of mechanical components.

6. The arrangement according to claim 5, wherein a second dispersion device is arranged before or after the second polarizing device for the spatial combination of radiation components which are changed and unchanged with respect to their polarization state.

7. An optical arrangement of a microscope for changing the spectral composition or intensity of specimen light, comprising:
   a light source provided in the microscope;
   a first polarizing device for spatial separation into radiation components of different polarization;
   a first dispersion device for spectral spatial splitting of at least one radiation component which are arranged before or after said first polarizing device;
   means for changing the polarization state of at least one part of the spectrally spatially split radiation component; and
   a second polarizing device for the spatial separation or combination of radiation components of different polarization
   wherein carrying out a spatial separation into radiation components of different polarizations with a first polarizing device or combining the radiation components of different polarization by a second polarizing device is adjustable in flexible manner without the movement of mechanical components.

8. The arrangement according to claim 7, wherein a spatially resolved detection of the specimen light is carried out.

9. The arrangement according to claim 7, wherein a second dispersion device is arranged before or after the second dispersion device for the spatial combination of radiation components which are changed and unchanged with respect to their polarization state.

10. An arrangement for the separation of illumination light and specimen light comprising:
    a light source provided in a microscope;
    a first polarizing device for spatial separation into radiation components of different polarization;
    a first dispersion device for spectral spatial splitting of at least one radiation component which are arranged before or after said first polarizing device;
    a means for changing a polarization state of at least one part of the spectrally spatially split radiation component; and
    a second polarizing device for the spatial separation or combination of radiation components of different polarization
    wherein carrying out a spatial separation into radiation components of different polarizations with a first polarizing device or combining the radiation components of different polarization by a second polarizing device is adjustable in flexible manner without the movement of mechanical components.

11. The arrangement according to claim 10, wherein a second dispersion device is arranged before or after the second polarizing device for the spatial combination of radiation components which are changed and unchanged with respect to their polarization state.

12. The arrangement according to claim 10, wherein an illumination of a specimen is carried out by a light source outside the arrangement for separation, and the specimen light is guided through the arrangement.

13. The arrangement according to claim 10, wherein a splitting of the illumination or specimen light into components which are polarized perpendicular to one another is carried out.

14. The arrangement according to claim 10, wherein the specimen light is detected at least partly by at least one detector.

15. The arrangement according to claim 10, wherein a laser is provided as illumination source.

16. The arrangement according to claim 10, wherein a white light source is provided as light source.

17. The arrangement according to claim 10, wherein an illumination with a plurality of wavelengths is carried out.

18. The arrangement according to claim 10, wherein fluorescent light or luminescent light or phosphorescent light or scattered light coming from the specimen is detected.

19. The arrangement according to claim 10, wherein the illumination light is changed with respect to its intensity or spectral composition during the image recording, so that different locations on the specimen are illuminated differently.

20. The arrangement according to claim 10, wherein imaging optics associated with first dispersion device are provided, which imaging optics image the spectral components in a focal plane, and the means for changing the polarization state of at least a part of the spectrally spatially split radiation component are arranged in the focal plane.

21. The arrangement according to claim 10, wherein the polarization state is changed by an SLM (spatial light modulator) which has controllable liquid crystal cells.

22. A widefield microscope comprising an arrangement according to claim 10.

23. A fluorescence microscope comprising an arrangement according to claim 10.

24. The fluorescence microscope according to claim 23, including means for carrying out a descanned, partially descanned or nondescanned detection.

25. A point-scanning laser scanning microscope comprising an arrangement according to claim 10.

26. A scanning microscope according to claim 25, including means for carrying out a descanned, partially descanned or nondescanned detection.

27. A line-scanning laser scanning microscope comprising an arrangement according to claim 10.

28. A scanning microscope according to claim 27, including means for carrying out a descanned, partially descanned or nondescanned detection.

29. A flow cytometer comprising an arrangement according to claim 10.

30. A parallel confocal microscope comprising an arrangement according to claim 10, comprising a pinhole array in an illumination beam path or detection beam path.

31. An arrangement according to claim 10, for imaging a periodic structure on an object, phase displacement of the structure and recording of phase-shifted images.

* * * * *